United States Patent
Wang et al.

(10) Patent No.: US 10,596,091 B2
(45) Date of Patent: Mar. 24, 2020

(54) HAIR COLOR-ALTERING COMPOSITIONS

(71) Applicant: L'OREAL, Paris (FR)

(72) Inventors: Jeffrey Wang, Jersey City, NJ (US); Lisa Jablonski, Edison, NJ (US); Joseph Kassman, Park Ridge, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/994,658

(22) Filed: May 31, 2018

(65) Prior Publication Data
US 2019/0365625 A1    Dec. 5, 2019

(51) Int. Cl.
| | |
|---|---|
| *A61Q 5/10* | (2006.01) |
| *A61K 8/49* | (2006.01) |
| *A61K 8/46* | (2006.01) |
| *A61K 8/41* | (2006.01) |
| *A61K 8/19* | (2006.01) |
| *A61K 8/06* | (2006.01) |
| *A61Q 5/06* | (2006.01) |
| *A61K 8/36* | (2006.01) |

(52) U.S. Cl.
CPC .............. *A61K 8/494* (2013.01); *A61K 8/068* (2013.01); *A61K 8/19* (2013.01); *A61K 8/36* (2013.01); *A61K 8/41* (2013.01); *A61K 8/46* (2013.01); *A61K 8/4973* (2013.01); *A61Q 5/065* (2013.01); *A61K 2800/4322* (2013.01)

(58) Field of Classification Search
CPC ........ A61Q 5/065; A61K 8/19; A61K 8/4973; A61K 2800/4322; A61K 8/447; A61K 8/068; A61K 2800/522; A61K 8/556; A61K 31/13
See application file for complete search history.

(56) References Cited

U.S. PATENT DOCUMENTS

| | | | |
|---|---|---|---|
| 6,730,789 B1 | 5/2004 | Birault | |
| 7,578,855 B2 | 8/2009 | Fadli | |
| 7,635,394 B2 | 12/2009 | Fadli | |
| 2008/0299059 A1* | 12/2008 | Quadir | A61K 8/11 424/61 |
| 2012/0210523 A1* | 8/2012 | Lalleman | A61K 8/34 8/408 |
| 2017/0035667 A1* | 2/2017 | Benn | A61K 8/41 |

FOREIGN PATENT DOCUMENTS

FR    2945739 A1 * 11/2010 ............... A61Q 5/10

OTHER PUBLICATIONS https://www.instacart.com/shop-n-save/products/16741022-Dark-and-Lovely-Fade-Resistant-Rich-Conditioning-Color-326-Berry-Burgundy-Haircolor-1-kt—Apr. 10, 2018.

* cited by examiner

*Primary Examiner* — Eisa B Elhilo
(74) *Attorney, Agent, or Firm* — Polsinelli PC (57) ABSTRACT

The present disclosure relates to color base compositions, as well as methods and kits using same. Certain compositions comprise:
(a) about 0.05 to about 10 wt. % of at least one 3-aminopyrazolo[1,5-a]pyridine;
(b) from about 0.01 to about 1 wt. % of a reducing agent other than thiolactic acid;
(c) from about 0.01 to about 5 wt. % of an ammonia compound;
(d) from about 5 to about 10 wt. % of an alkanolamine;
(e) from about 0.01 to about 6 wt. % of a carboxylic acid-containing surfactant; and
(f) from about 0.01 to about 1 wt. % of an antioxidant.

19 Claims, 2 Drawing Sheets

Permed Swatches

HAIR COLOR-ALTERING COMPOSITIONS

FIELD

The present disclosure generally relates to compositions for use in coloring the hair.

BACKGROUND

The process of changing the color of hair, can involve depositing an artificial color onto the hair which provides a different shade or color to the hair, and/or lifting the color of the hair, such as lightening the color of dark hair to lighter shades.

In general, hair lightening or color lifting compositions and hair dyeing compositions possess an alkalinity such that these compositions have a pH value of above 7, typically being at pH 9 and above, and may generally require the presence of an alkalizing agent such as ammonia or an ammonia gas-generating compound and/or an amine or ammonium-based compound in amounts sufficient to make such compositions alkaline. This alkalizing agent causes the hair shaft to swell, thus allowing active agents into the hair.

Imparting a color change or color effect on hair can be done using permanent and semi-permanent or temporary hair coloring products. Conventional permanent hair coloring products are dye compositions comprising oxidation dye precursors, which are also known as primary intermediates or couplers. These oxidation dye precursors are colorless or weakly colored compounds which, when combined with oxidizing products, give rise to colored complexes by a process of oxidative condensation. The oxidizing products conventionally use peroxides such as hydrogen peroxide as oxidizing agents. Such permanent hair color products also contain alkalizing agents which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. In contrast, semi-permanent dyeing uses direct dyes, which are nonionic or ionic dyes and colored compounds capable of producing a more or less pronounced change of the natural color of the hair, resistant to shampoo-washing several times. These dyes may or may not be used in the presence of an oxidizing agent. In contrast with oxidation dye precursors, a direct dye is a relatively voluminous molecule that does not penetrate easily into the core of the fiber.

Consumers are always looking for new shades of hair color, which can be obtained by known dye molecules. However, one issue that can occur with these relatively complex dye molecules is that they can be difficult to formulate into stable hair color base. Thus, it would therefore be desirable to provide the consumer with stable hair color-altering compositions that allow for shades not previously attainable.

SUMMARY

One aspect of the invention pertains to a hair color-altering composition comprising:
(a) about 0.05 to about 10 wt. % of at least one 3-aminopyrazolo[1,5-a]pyridine;
(b) from about 0.01 to about 1 wt. % of a reducing agent other than thiolactic acid;
(c) from about 0.01 to about 5 wt. % of an ammonia compound;
(d) from about 5 to about 10 wt. % of an alkanolamine;
(e) from about 0.01 to about 6 wt. % of a carboxylic acid-containing surfactant; and
from about 0.01 to about 1 wt. % of an antioxidant.

In one or more embodiments, the hair color base is in the form of a microemulsion. In some embodiments, the at least one 3-aminopyrazolo[1,5-a]pyridine is present in an amount of about 0.4 to about 2.5 wt. %. In one or more embodiments, the at least one 3-aminopyrazolo[1,5-a]pyridine comprises 2-[(3-aminopyrazolo[1,5-a]pyridin-2-yl)oxy]ethanol hydrochloride. In some embodiments, the at least one 3-aminopyrazolo[1,5-a]pyridine comprises 4-(3-Aminopyrazolo[1,5-a]pyridin-2-yl)-1,1-dimethyl-piperazin-1-ium or a salt thereof. In one or more embodiments, the reducing agent comprises a monovalent thiolactate salt. In some embodiments, the monovalent thiolactate salt comprises ammonium thiolactate. In one or more embodiments, the ammonia compound comprises ammonium hydroxide. In some embodiments, the alkanolamine is present in an amount of from about 5 to about 8 wt. %. In one or more embodiments, the alkanolamine comprises monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane, and combinations thereof. In some embodiments, the alkanolamine comprises monoethanolamine. In one or more embodiments, the antioxidant comprises ascorbic acid, sodium sulfite, sodium metabisulfite, sodium hydrosulfite, tocopherols, alpha-tocopherol, tocopheryl acetate, panthenol, selenium sulfide, zinc formosulfoxylate, isoascorbic acid, magnesium ascorbyl phosphate, ascorbyl glucoside, cysteine, thiourea, glyceryl monothioglycolate, thioglycerol, 2,5-dihydroxybenzoic acid, erythorbic acid and combinations thereof. In some embodiments, the carboxylic acid-containing surfactant comprises laureth-11 carboxylic acid, laureth-5 carboxylic acid, and combinations thereof. In one or more embodiments, the composition is essentially free of a polyquaternium polymer. In some embodiments, the composition is essentially free of polyquaternium-6. In one or more embodiments, the composition is stable for at least one month. In some embodiments, the composition is essentially free of thiolactic acid.

In one or more embodiments, the hair color altering composition comprises:
(a) about 0.05 to about 10 wt. % of 2-[(3-aminopyrazolo[1,5-a]pyridin-2-yl)oxy]ethanol hydrochloride;
(b) from about 0.01 to about 1 wt. % of ammonium thiolactate;
(c) from about 0.01 to about 5 wt. % of ammonia;
(d) from about 5 to about 10 wt. % of an monoethanolamine;
(e) from about 0.01 to about 6 wt. % of laureth-5 carboxylic acid; and
(f) from about 0.01 to about 1 wt. % of erythorbic acid.

Another aspect of the invention pertains to kits. Said kits may comprise the hair color-altering compositions described herein and a developer composition. The developer composition generally comprises one or more oxidizing agents.

Another aspect of the invention pertains to methods of using the hair color-altering compositions described herein. The methods comprise applying the hair color altering compositions to hair.

DETAILED DESCRIPTION

One aspect of the invention relates to hair color-altering compositions. In one or more embodiments, the hair color-altering compositions comprise:

(a) about 0.05 to about 10 wt. % of at least one 3-aminopyrazolo[1,5-a]pyridine;

(b) from about 0.01 to about 1 wt. % of a reducing agent other than thiolactic acid;

(c) from about 0.01 to about 5 wt. % of ammonia compound;

(d) from about 5 to about 10 wt. % of an alkanolamine;

(e) from about 0.01 to about 6 wt. % of a carboxylic acid-containing surfactant; and (f) from about 0.01 to about 1 wt. % of an antioxidant.

It has been surprisingly discovered that 3-aminopyrazolo[1,5-a]pyridine dye compounds can be stabilized with the above combination of ingredients. The stabilization allows for increased dye loads of 3-aminopyrazolo[1,5-a]pyridine, and thus allows for the possibility of new color shades not previously available. Also, with increased dye loads, it becomes possible to produce higher tenacity shades. As used herein, the term "stable" means the hair color-altering composition does not separate and remains viable for use to color the hair.

3-aminopyrazolo[1,5-a]pyridine

The hair color-altering compositions described herein contain at least one 3-aminopyrazolo[1,5-a]pyridine. As used herein, the term "3-aminopyrazolo[1,5-a]pyridine" includes derivatives of 3-aminopyrazolo[1,5-a]pyridine, which are further described below. These compounds are known dye molecules which can provide color to the hair when combined with oxidizing products.

As described above, the 3-aminopyrazolo[1,5-a]pyridine can be stabilized such that higher concentrations can be used than previously known. Thus, the 3-aminopyrazolo[1,5-a]pyridine may be present in amounts ranging from about 0.05, 0.06, 0.07, 0.08, 0.09, 0.1, 0.15, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 or 2.0 to about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 5.5, 6.0, 6.5, 7.0, 7.5, 8.0, 8.5, 9.0, 9.5 or 10 wt %.

In one or more embodiments, the at least one 3-aminopyrazolo[1,5-a]pyridine has a structure represented by formula (I) below as oxidation base and/or one of its addition salts with an acid or with a base:

in which:

R1, R2, R3, R4 and R5, which are identical or different, represent a hydrogen or halogen atom; an —NHSO3H radical; a hydroxyl radical; a (C1-C4)alkyl radical; a (C1-C4)alkoxy radical; a (C1-C4)alkylthio radical; mono(C1-C4)alkylamino; a di(C1-C4)alkylamino radical in which the two alkyl groups, in conjunction with the nitrogen atom to which they are bonded, may form a ring which may be interrupted by one or more nitrogen, oxygen or sulfur atoms; a heterocycle; a nitro radical; a phenyl radical; a carbonyl radical; a ((C1-C4)alkoxy)carbonyl radical; a carboxamido radical; a cyano radical; an amino radical; a sulfonyl radical; a —CO2H radical, an —SO3H radical; a —PO3H2 radical; a —PO4H2 radical; or a group of formula (II) below:

in which R represents an oxygen or nitrogen atom, X represents an oxygen atom or an NH or NH(C1-C4)alkyl group, and Y represents a hydroxyl, amino, C1-C4 alkyl, (C1-C4)alkoxy, (C1-C4)alkylamino or di(C1-C4)alkylamino radical. This class of 3-aminopyrazolo[1,5-a]pyridine are described in U.S. Pat. No. 6,730,789, the contents of which are incorporated by reference.

In the compounds of formula (I) above, the alkyl term used for the alkyl radicals and for the groups containing an alkyl moiety signifies a linear or branched carbon chain containing 1 to 4 carbon atoms which is unsubstituted or substituted by one or more heterocycles or by one or more phenyl groups or by one or more groups selected from halogen atoms such as chlorine, bromine, iodine and fluorine; hydroxyl, alkoxy, amino, carbonyl, carboxamido, sulfonyl, —CO$_2$H, —SO$_3$H, —PO$_3$H$_2$, —PO$_4$H$_2$, —NHSO$_3$H, sulfonamide, monoalkyl (C$_1$-C$_4$)amino or trialkyl(C$_1$-C$_4$) ammonium radicals or else by a dialkyl(C$_1$-C$_4$)amino radical in which the two alkyl groups, in conjunction with the nitrogen atom of said dialkyl(C$_1$-C$_4$)amino group to which they are bonded, may form a ring which may be interrupted by one or more nitrogen, oxygen or sulfur atoms.

Similarly, the alkoxy term used for the alkoxy radicals and for the groups containing an alkoxy moiety signifies a linear or branched O-carbon chain containing 1 to 4 of carbon, which is unsubstituted or substituted by one or more groups selected from heterocycles; halogen atoms such as chlorine, bromine, iodine and fluorine; hydroxyl, amino, carbonyl, carboxamido, sulfonyl, —CO$_2$H, —SO$_3$H, —PO$_3$H$_2$, —PO$_4$H$_2$, —NHSO$_3$H, sulfonamide, monoalkyl(C$_1$-C$_4$) amino or trialkyl(C$_1$-C$_4$)ammonium radicals or else by a dialkyl(C$_1$-C$_4$)amino radical in which the two alkyl groups, in conjunction with the nitrogen atom of said dialkyl($C_1$-$C_4$)amino group to which they are bonded, may form a ring which may be interrupted by one or more nitrogen, oxygen or sulfur atoms.

As claimed in the invention, a heterocycle is an aromatic or nonaromatic ring containing 5, 6 or 7 members and from 1 to 3 heteroatoms selected from nitrogen, sulfur and oxygen atoms. These heterocycles can be condensed with other heterocycles or with a phenyl group. They can be substituted by a halogen atom; a ($C_1$-$C_4$)alkyl radical; a ($C_1$-$C_4$)alkoxy radical; a hydroxyl radical; an amino radical; a ($C_1$-$C_4$) alkylamino radical; di($C_1$-$C_4$)alkylamino in which the two alkyl groups, in conjunction with the nitrogen atom to which they are bonded, may form a ring which may be interrupted by one or more nitrogen, oxygen or sulfur atoms. These heterocycles may additionally be quaternized by a ($C_1$-$C_4$) alkyl radical.

Among these heterocycles, mention may be made in particular, by way of example, of the following rings: thiadiazole, triazole, isoxazole, oxazole, azaphosphole, thiazole, isothiazole, imidazole, pyrazole, triazine, thiazine, pyrazine, pyridazine, pyrimidine, pyridine, diazepin, oxazepin, benzotriazole, benzoxazole, benzimidazole, benzothiazole, morpholine, piperidine, piperazine, azetidine, pyrrolidine, aziridine, 3-(2-hydroxyethyl)benzothiazol-3-ium and 1-(2-hydroxyethyl)pyridinium.

As claimed in the invention, phenyl means a phenyl radical which is unsubstituted or substituted by one or more cyano, carbonyl, carboxamido, sulfonyl, —$CO_2H$, —$SO_3H$, —$PO_3H_2$, —$PO_4H_2$, hydroxyl, amino, monoalkyl($C_1$-$C_4$)amino or dialkyl($C_1$-$C_4$)amino radicals in which the two alkyl groups, in conjunction with the nitrogen atom of said dialkyl($C_1$-$C_4$)amino group to which they are bonded, may form a ring which may be interrupted by one or more nitrogen, oxygen or sulfur atoms.

Among the groups of formula (II) above, mention may be made in particular of the groups acetamide, dimethylurea, O-methylcarbamate, methylcarbonate, N-dimethylcarbamate and the esters.

Among the compounds of formula (I) above, preference is given to 3-aminopyrazolo[1,5-a]pyridines of subformula (Ia) below and their addition salts with an acid or with a base:

(Ia)

in which:

$R_1$, $R_2$ and $R_3$, which are identical or different, represent a hydrogen or halogen atom; a hydroxyl radical; a ($C_1$-$C_4$) alkyl radical; a ($C_1$-$C_4$)alkylthio radical; a ($C_1$-$C_4$)alkoxy radical; an —NHSO3H radical; an amino radical; a ($C_1$-$C_4$) alkylamino radical; a di($C_1$-$C_4$)alkylamino radical in which the two alkyl groups, in conjunction with the nitrogen atom to which they are bonded, may form a ring which may be interrupted by one or more nitrogen, oxygen or sulfur atoms; a heterocycle as defined above; a sulfonamide radical; a carbonyl radical; a (($C_1$-$C_4$)alkoxy)carbonyl radical; a carboxamido radical; or a group of formula (II) above, in which R represents an oxygen or nitrogen atom, X represents an oxygen atom or an NH or NH($C_1$-$C_4$)alkyl group, and Y represents a hydroxyl, amino, $C_1$-$C_4$ alkyl, ($C_1$-$C_4$)alkoxy, ($C_1$-$C_4$)alkylamino or di($C_1$-$C_4$)alkylamino radical.

Among the 3-aminopyrazolo[1,5-a]pyridines of formula (I) which can be used as oxidation bases in the dyeing compositions of the invention, mention may be made in particular of:
pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2-carboxylic acid;
2-methoxypyrazolo[1,5-a]pyridin-3-ylamin;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl)-(2-hydroxyethyl) amino]ethanol;
2-[(3-aminopyrazolo[1,5-a]pyridin-7-yl)-(2-hydroxyethyl) amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
and their addition [lacuna] with an acid or with a base.

The great majority of the 3-aminopyrazolo[1,5-a]pyridines of formula (I) are compounds which are known in the pharmaceutical field and are described in particular in the U.S. Pat. No. 5,457,200. These compounds can be prepared by synthesis methods which are known in the literature, such as are described, for example, in the U.S. Pat. No. 5,457,200.

In some embodiments, the at least one 3-aminopyrazolo [1,5-a]pyridine has a structure represented by formula (III) below and salts and solvates thereof:

(III)

in which:

$Z_1$ is chosen from an oxygen atom and a group $NR_6$; when $Z_1$ represents $NR_6$, $R_1$ and $R_6$ can form, together with the nitrogen atom to which they are attached, a saturated, unsaturated or aromatic heterocycle with 5 to 8 ring members, optionally substituted, $Z_1$ can also be a divalent radical chosen from S, SO, and $SO_2$ when $R_1$ is a methyl radical,

$R_1$ and $R_2$ are chosen from, independently:
a hydrogen atom,
$C_1$-$C_{10}$ alkyl radicals, optionally substituted, and the substituent can optionally be a saturated, unsaturated or aromatic (hetero)cycle with 5 to 8 ring members, optionally substituted, saturated, unsaturated or aromatic (hetero)cycles with 5 to 8 ring members, optionally substituted,

$R_3$, $R_4$, and $R_5$, independently, are chosen from:
a hydrogen atom,
$C_1$-$C_4$ alkyl radicals, optionally substituted,
an entity chosen from $NH_2$, $NHR_{10}$, $NR_{11}R_{12}$, OH, and $OR_9$, wherein $R_9$ and $R_{10}$, which may be identical or different are chosen from linear or branched $C_1$-$C_6$ alkyl groups, optionally substituted; $R_{11}$ and $R_{12}$, which may be identical or different, are chosen from linear or branched $C_1$-$C_6$ alkyl groups, optionally substituted; and $R_{11}$ and $R_{12}$ can form, together with the nitrogen atom to which they are attached, a saturated, unsaturated or aromatic heterocycle with 5 to 8 ring members optionally containing at least one other heteroatom or group chosen from N, O, S, $SO_2$, and CO, the heterocycle being optionally substituted, $R_2$, $R_3$, $R_4$, $R_5$ can form, two by two with the adjacent radicals, saturated or unsaturated (hetero)cycles, optionally substituted.

In one or more embodiments, the 2-methoxypyrazolo[1,5-a]pyridin-3-ylamine and 2-morpholino-pyrazolo[1,5-a]pyridin-3-ylamine respectively with the following formulae are excluded:

2-Methoxypyrazolo[1,5-a]pyridin-3-ylamine

2-Morpholin-4-yl-pyrazolo[1,5-a]-pyridin-3-ylamine

According to at least one embodiment of the present disclosure, the oxidation base of formula (III) above is such that $Z_1$ is chosen from an oxygen atom, a radical $NR_6$ and a radical $NR_6$ forming a heterocycle with $R_1$.

According to at least one embodiment, the radical $R_1$ can be chosen from an alkyl radical, an alkyl radical substituted with a hydroxy, an alkyl radical substituted with an amino or (di)alkylamino, an alkyl radical substituted with a nitrogen-containing heterocycle, for example piperazinyl, imidazolyl, pyrrolidinyl, pyridinyl, morpholinyl, and piperidinyl. According to one embodiment, the alkyl radical has from 1 to 6 carbon atoms.

Radical $R_6$ can be chosen from a hydrogen atom, an alkyl radical or an alkyl radical-substituted with a hydroxy radical, an amino radical, an alkylamino radical, a dialkyl amino radical, an alkyl radical substituted with a nitrogen-containing heterocycle, for example piperazinyl, imidazolyl, pyrrolidinyl, pyridinyl, morpholinyl, and piperidinyl. According to one embodiment, $R_6$ has from 1 to 6 carbon atoms.

According to at least one embodiment in which $R_1$ and $R_6$ together form a heterocycle with the nitrogen atom to which they are attached, the heterocycle can then be chosen from imidazoles, piperazines, pyrrolidines, and diazapanes, and these heterocycles can be substituted or unsubstituted.

When $R_2$, $R_3$, $R_4$ and $R_5$ represent a substituted alkyl radical, this alkyl radical can then be substituted, in at least one embodiment, by radical chosen from —OH, —$OR_9$, —$NH_2$, —$NHR_{10}$, —$NR_{11}R_{12}$ and $SR_9$ in which $R_9$, $R_{10}$, $R_{11}$ and $R_{12}$, which may be identical or different, are as defined previously.

Mention may be made, as examples, of methyl, ethyl, hydroxyethyl, aminoethyl, propyl and butyl radicals. According to at least one embodiment, $R_2$, $R_3$, $R_4$ and $R_5$ are chosen from, independently, a hydrogen atom and $C_1$-$C_4$ alkyl radicals such as methyl, ethyl, propyl, isopropyl, butyl, tert-butyl, or $R_4$ and $R_5$ together form a (hetero)cycle with 5 to 8 ring members. According to one embodiment, $R_4$ and $R_5$ together form a saturated or unsaturated ring with 5 or 8 ring members, such as from 5 to 6 ring members, for example a cyclopentane or cyclohexane, optionally substituted.

The following compounds may be mentioned as useful herein:
N-2-ethylpyrazolo[1,5-a]pyridine-2,3-diamine dihydrochloride,
2-(3-aminopyrazolo[1,5-a]pyridin-2-ylamino)ethanol dihydrochloride,
1-(3-aminopyrazolo[1,5-a]pyridin-2-ylamino)propan-2-ol dihydrochloride,
N-2-(3-imidazol-1-ylpropyl)pyrazolo[1,5-a]pyridine-2,3-diamine dihydrochloride,
2-pyrrolidin-1-ylpyrazolo[1,5-a]pyridin-3-ylamine dihydrochloride,
2-(3-dimethylaminopyrrolidin-1-yl)pyrazolo[1,5-a]pyridin-3-ylamine dihydrochloride,
2-imidazol-1-ylpyrazolo[1,5-a]pyridin-3-ylamine dihydrochloride,
N-2-(2-pyrrolidin-1-ylethyl)pyrazolo[1,5-a]pyridine-2,3-diamine dihydrochloride,
2-(3-aminopyrazolo[1,5-a]pyridin-2-yloxy)ethanol dihydrochloride,
2-ethoxypyrazolo[1,5-a]pyridin-3-ylamine dihydrochloride,
2-methoxy-7-methylpyrazolo[1,5-a]pyridin-3-ylamine hydrochloride,
4-ethyl-2-methoxy-7-methylpyrazolo[1,5-a]pyridin-3-ylamine dihydrochloride,
4-ethyl-7-methyl-2-pyrrolidin-1-ylpyrazolo[1,5-a]pyridin-3-ylamine dihydrochloride,
N-2-(2-piperidin-1-ylethyl)pyrazolo[1,5-a]pyridine-2,3-diamine dihydrochloride,
N-2-2-(diisopropylamino)ethyl]pyrazolo[1,5-a]pyridine-2,3-diamine dihydrochloride,
N-2-[2-(diethylamino)ethyl]pyrazolo[1,5-a]pyridine-2,3-diamine dihydrochloride,
N-2-(2-pyridin-3-ylethyl)pyrazolo[1,5-a]pyridine-2,3-diamine dihydrochloride,
N-2-(2-pyridin-4-ylethyl)pyrazolo[1,5-a]pyridine-2,3-diamine dihydrochloride,
N-2-(2-pyridin-2-ylethyl)pyrazolo[1,5-a]pyridine-2,3-diamine dihydrochloride,
N-2-(2-piperazin-1-ylethyl)pyrazolo[1,5-a]pyridine-2,3-diamine dihydrochloride,
N-2-[2-(4-methylpiperazin-1-yl)ethyl]pyrazolo[1,5-a]pyridine-2,3-diamine dihydrochloride,
N-2-(2-morpholin-4-ylethyl)pyrazolo[1,5-a]pyridine-2,3-diamine dihydrochloride,
N-2-[2-(dimethylamino)ethyl]-7,8-dihydro-6H-cyclopenta[e]pyrazolo[1,5-a]pyridine-2,3-diamine dihydrochloride,
2-[(3-amino-7,8-dihydro-6H-cyclopenta[e]pyrazolo[1,5-a]pyridin-2-yl)amino]ethanol hydrochloride,
2-methoxy-7,8-dihydro-6H-cyclopenta[e]pyrazolo[1,5-a]pyridin-3-amine hydrochloride,
2-isopropoxy-7,8-dihydro-6H-cyclopenta[e]pyrazolo[1,5-a]pyridin-3-amine hydrochloride,
2-[2-(dimethylamino)ethoxy]pyrazolo[1,5-a]pyridin-3-amine dihydrochloride,
2-(2-pyrrolidin-1-ylethoxy)pyrazolo[1,5-a]pyridin-3-amine dihydrochloride, 2-(2-piperidin-1-ylethoxy)pyrazolo[1,5-a]pyridin-3-amine dihydrochloride,
2-(2-morpholin-4-ylethoxy)pyrazolo[1,5-a]pyridin-3-amine dihydrochloride,
2-[2-(diisopropylamino)ethoxy]pyrazolo[1,5-a]pyridin-3-amine dihydrochloride,
2-(2-pyridin-2-ylethoxy)pyrazolo[1,5-a]pyridin-3-amine dihydrochloride,
2-(2-pyridin-3-ylethoxy)pyrazolo[1,5-a]pyridin-3-amine dihydrochloride,
2-(2-pyridin-4-ylethoxy)pyrazolo[1,5-a]pyridin-3-amine dihydrochloride,
N-5,N-5-dimethyl-2-methylsulphanylpyrazolo[1,5-a]pyridine-3,5-diamine dihydrochloride.

In further embodiments, the at least one 3-aminopyrazolo[1,5-a]pyridine comprises 2-(3-aminopyrazolo[1,5-a]pyridin-2-yloxy)ethanol dihydrochloride, which has a structure represented by formula (IIIa):

(IIIa)

The compounds of formula (III) can be prepared by synthesis methods which are known in the literature, such as are described, for example, in the U.S. Pat. No. 7,635,394.

In some embodiments, the at least one 3-aminopyrazolo[1,5-a]pyridine has a structure represented by formula (IV), as well as its salts and solvates:

(IV)

in which
$Z_1$ and $Z_2$, which may be the same or different, are independently chosen from
a single covalent bond,
a divalent radical chosen from
an oxygen atom;
a radical $—NR_6(R_7)_p—$, with p=0 or 1, wherein:
when p is equal to 0, $R_6$ is chosen from a hydrogen atom and $C_1$-$C_6$ alkyl radicals, or $R_6$ together with at least one of $R_1$ and $R_2$ form, together with the nitrogen atom to which they are attached, a substituted or unsubstituted, saturated or unsaturated, aromatic or non-aromatic heterocycle comprising 5 to 8 ring members, wherein said heterocycle may contain at least one heteroatom chosen from N, O, S, $SO_2$, and —CO—, and may be cationic and/or substituted with a cationic or non-cationic radical;

When p is equal to 1, $—NR_6R_7—$ is a cationic radical in which $R_6$ and $R_7$, may be the same or different, and are independently chosen from alkyl radicals; and
when $R_1$ is a methyl radical, $Z_1$ may also be chosen from a divalent radical —S—, —SO— and —$SO_2$—;
with the proviso that at least one of $Z_1$ and $Z_2$ is not a single covalent bond;
$R_1$ and $R_2$, which may be the same or different, are independently chosen from:
a hydrogen atom;
a $C_1$-$C_{10}$ alkyl radical, optionally substituted and optionally interrupted by a heteroatom or a group chosen from O, N, Si, S, SO and $SO_2$;
a $C_1$-$C_{10}$ alkyl radical substituted and/or interrupted by a cationic radical;
a halogen atom;
an $SO_3H$ radical;
a ring with 5 to 8 ring members, wherein said ring may be substituted or unsubstituted, saturated, unsaturated or aromatic, and may contain at least one heteroatom or group chosen from N, O, S, $SO_2$, —CO—, and said ring may be cationic and/or substituted with a cationic radical; and
when at least one of $Z_1$ or $Z_2$ is a covalent bond, then $R_1$ or $R_2$ respectively may be also be a radical chosen from:
optionally substituted $C_1$-$C_6$ alkylcarbonyls; and
—O—CO—R, —CO—O—R, NR—CO—R' and —CO—NRR' in which R and R' may be the same or different, and are independently chosen from a hydrogen atom and optionally substituted $C_1$-$C_6$ alkyl radicals;
$R_3$, $R_4$ and $R_5$, which may be the same or different, are independently chosen from:
a hydrogen atom;
a hydroxyl radical;
a $C_1$-$C_6$ alkoxy radical;
a $C_1$-$C_6$ alkylthio radical;
an amino radical;
a monoalkylamino radical;
a $C_1$-$C_6$ dialkylamino radical, in which the alkyl radicals can form, together with the nitrogen atom to which they are attached, a heterocycle with 5 to 8 ring members, wherein said heterocycle may be saturated or unsaturated, aromatic or non-aromatic, and may contain at least one heteroatom or groups chosen from N, O, S, $SO_2$, CO, and said heterocycle may be cationic and/or substituted with a cationic radical;
an optionally substituted $C_1$-$C_6$ alkylcarbonyl radical;
a radical chosen from —O—CO—R, —CO—O—R, NR—CO—R' and —CO—NRR' radicals, in which R and R' may be the same or different, and are independently chosen from a hydrogen atom and optionally substituted $C_1$-$C_6$ alkyl radicals;
a halogen atom;
a radical —$NHSO_3H$;
an optionally substituted $C_1$-$C_4$ alkyl radical;
an optionally substituted, saturated, unsaturated or aromatic carbon ring; and
any two of $R_3$, $R_4$ and $R_5$ can form a saturated or unsaturated ring;
X is chosen from at least one anion that can ensure electronegativity of the derivative of formula (I),
with the proviso that at least one of $Z_1$, $R_1$, $Z_2$ and $R_2$ represents a cationic radical.

The following substituents may be mentioned as non-limiting examples of substituents of these alkyl radicals: halo; hydroxy; alkoxy; amino; thio, alkylthio, $C_1$-$C_6$ alkylamino; $C_1$-$C_6$ dialkylamino in which the alkyl radicals can form, together with the nitrogen atom to which they are attached, a heterocycle with 5 to 8 ring members, saturated, unsaturated, aromatic or non-aromatic, cationic or non-cationic, and which may contain at least one heteroatom or group selected from N, O, S, $SO_2$, CO, and the heterocycle may be substituted; alkyl($C_1$-$C_6$)carbonyl; —O—CO—R; —CO—O—R; NR—CO—R' or —CO—NRR' in which R and R' are as defined previously; and a quaternary ammonium radical as defined previously.

This applies to the alkyl radicals present in any one of the radicals defined in formula (I), for example, the alkoxy (alkyl-O—) or alkylthio radicals.

As examples of substituents of the rings or heterocycles, non-limiting mention is made of alkyl radicals, substituted alkyl radicals, hydroxy, alkoxy, amino, alkylamino, and dialkylamino radicals.

As used herein, the term "cationic radical," means any linear or branched radical bearing a quaternary ammonium, this quaternary ammonium being of the type —$N^+R_{17}R_{18}R_{19}$, $R_{17}$, $R_{18}$, $R_{19}$, in which $R_{17}$-$R_{19}$ may be the same or different, and are chosen from $C_1$-$C_6$ alkyl radicals which may be substituted with a hydroxy.

As used herein, a cationic ring or heterocycle refers to a ring containing a quaternary ammonium.

As examples of radicals of the type —$N^+R_{17}R_{18}R_{19}$ which may be utilized in the present disclosure, non-limiting mention is made of trimethylammonium, triethylammonium, dimethyl-ethyl ammonium, diethyl-methylammonium, diisopropylmethylammonium, diethyl-propyl ammonium, hydroxyethyl diethyl ammonium, di-beta-hydroxyethylmethylammonium and tri-beta-hydroxyethylammonium radicals.

As non-limiting examples of cationic heterocycles that may be utilized in the present disclosure, mention is made of the imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, triazoliums and benzoxazoliums.

The compounds of formula (I) may optionally be salified by strong mineral acids, including, for example, HCl, HBr, HI, $H_2SO_4$ and $H_3PO_4$, or by organic acids such as, for example, acetic, lactic, tartaric, citric or succinic, benzenesulphonic, para-toluenesulphonic, formic and methanesulphonic acid.

The compounds of formula (IV) may also be in the form of solvates, for example a hydrate or a solvate of a linear or branched alcohol such as ethanol or isopropanol. Of course, other solvents may also be utilized.

As used herein, the term "derivative" of formula (IV) means all mesomeric or isomeric forms.

As non-limiting examples of derivatives of formula (IV), mention is made of the following compounds, in which $X^-$ is as defined previously:

[2-(3-Amino-pyrazolo[1,5-a]pyridin-2-ylamino)-ethyl]-trimethyl-ammonium

3-(3-Amino-pyrazolo[1,5-a]pyridin-2-yl)-1-methyl-3H-imidazol-1-ium

[2-(3-Amino-pyrazolo[1,5-a]pyridin-2-ylamino)-ethyl]-ethyl-dimethyl-ammonium

[2-(3-Amino-pyrazolo[1,5-a]pyridin-2-ylamino)-ethyl]-(2-hydroxy-ethyl)-dimethyl-ammonium

[3-(3-Amino-pyrazolo[1,5-a]pyridin-2-ylamino)-propyl]-trimethyl-ammonium

3-[3-(3-Amino-pyrazolo[1,5-a]pyridin-2-ylamino)-propyl]-1-methyl-3H-imidazol-1-ium 3-[3-(3-Amino-pyrazolo[1,5-a]pyridin-2-ylamino)-propyl]-1-(2-hydroxy-ethyl)-3H-imidazol-1-ium

-continued

3-[2-(3-Amino-pyrazolo[1,5-a]pyridin-2-yloxy)-ethyl]-
1-(2-hydroxy-ethyl)-3H-imidazol-1-ium

1-{2-[(3-aminopyrazolo[1,5-a]pyridin-2-yl)oxy]ethyl}-
1-methylpyrrolidinium

1-{2-[(3-aminopyrazolo[1,5-a]pyridin-2-yl)oxy]ethyl}-
1-methylpiperidinium

4-{2-[(3-aminopyrazolo[1,5-a]pyridin-2-yl)oxy]ethyl}-
4-methylmorpholin-4-ium 2-[(3-aminopyrazolo[1,5-a]pyridin-2-yl)oxy]-
N,N,N-trimethylethanaminium N-{2-[(3-aminopyrazolo[1,5-a]pyridin-2-yl)oxy]ethyl}-
N-isopropyl-N-methylpropan-2-aminium 1-(3-aminopyrazolo[1,5-a]pyridin-2-yl)-1-
methylpyrrolidinium

-continued

[1-(3-Amino-pyrazolo[1,5-a]pyridin-2-yl)-pyrrolidin-3-yl]-
trimethyl-ammonium

4-(3-Amino-pyrazolo[1,5-a]pyridin-2-yl)-1,1-
dimethyl-piperazin-1-ium

4-[2-(3-Amino-pyrazolo[1,5-a]pyridin-2-ylamino)-
ethyl]-1,1-dimethyl-piperazin-1-ium

4-[2-(3-Amino-pyrazolo[1,5-a]pyridin-2-ylamino)-
ethyl]-1-methyl-1-propyl-piperazin-1-ium 4-(3-Amino-pyrazolo[1,5-a]pyridin-2-yl)-
1-(2-hydroxy-ethyl)-piperazin-1-ium

[4-(3-Amino-pyrazolo[1,5-a]pyridin-2-ylamino)-
phenyl]-trimethyl-ammonium

3-[3-(3-Amino-pyrazolo[1,5-a]pyridin-2-yloxy)-
propyl]-1-methyl-3H-imidazol-1-ium

-continued

4-(3-Amino-pyrazolo[1,5-a]pyridin-2-yl)-
1,1-dimethyl-[1,4]diazepan-1-ium

[2-(3-Amino-6,7-dimethyl-pyrazolo[1,5-a]pyridin-2-
ylamino)-ethyl]-trimethyl-ammonium

4-(3-Amino-6,7-dimethyl-pyrazolo[1,5-a]pyridin-2-
yl)-1,1-dimethyl-piperazin-1-ium

4-(3-Amino-6,7-dimethyl-pyrazolo[1,5-a]pyridin-2-
yl)-1-(2-hydroxy-ethyl)-1-methyl-piperazin-1-ium

[1-(3-Amino-6,7-dimethyl-pyrazolo[1,5-a]pyridin-2-
yl)-pyrrolidin-3-yl]-trimethyl-ammonium 1-(3-amino-6,7-dimethylpyrazolo[1,5-a]pyridin-2-
yl)-methylpyrrolidinium

[1-(3-Amino-6,7-dimethyl-pyrazolo[1,5-a]pyridin-2-
yl)-pyrrolidin-3-yl]-(2-hydroxy-ethyl)-dimethyl-ammonium

-continued

{1-[2-(3-Amino-6,7-dimethyl-pyrazolo[1,5-a]pyridin-2-yloxy)-
ethyl]-pyrrolidin-3-yl}-trimethyl-ammonium

1-{2-[(3-amino-6,7-dimethylpyrazolo[1,5-a]pyridin-2-
yl)oxy]ethyl}-1-methylpyrrolidinium

1-{2-[(3-amino-6,7-dimethylpyrazolo[1,5-a]pyridin-2-
yl)oxy]ethyl}-1-methylpiperidinium

4-{2-[(3-amino-6,7-dimethylpyrazolo[1,5-a]pyridin-2-
yl)oxy]ethyl}-4-methylmorpholin-4-ium

2-[(3-amino-6,7-dimethylpyrazolo[1,5-a]pyridin-2-
yl)oxy]-N,N,N-trimethylethanaminium

N-{2-[(3-amino-6,7-dimethylpyrazolo[1,5-a]pyridin-2-yl)oxy]ethyl}-N-isopropyl-N-methylpropan-2-aminium

[3-(3-Amino-6,7-dimethyl-pyrazolo[1,5-a]pyridin-2-ylamino)-propyl]-trimethyl-ammonium

[3-(3-Amino-6,7-dimethyl-pyrazolo[1,5-a]pyridin-2-yloxy)-propyl]-trimethyl-ammonium

2-[(3-amino-7,8-dihydro-6H-cyclopenta[e]pyrazolo[1,5-a]pyridin-2-yl)oxy]-N,N,N-trimethylethanaminium

2-[(3-amino-7,8-dihydro-6H-cyclopenta[e]pyrazolo[1,5-a]pyridin-2-yl)amino]-N,N,N-trimethylethanaminium

3-[(3-amino-7,8-dihydro-6H-cyclopenta[e]pyrazolo[1,5-a]pyridin-2-yl)amino]-N,N,N-trimethylpropan-1-aminium

1-{2-[(3-amino-7,8-dihydro-6H-cyclopenta[e]pyrazolo[1,5-a]pyridin-2-yl)amino]ethyl}-3-methyl-1H-imidazol-3-ium

1-{3-[(3-amino-7,8-dihydro-6H-cyclopenta[e]pyrazolo[1,5-a]pyridin-2-yl)amino]propyl}-3-methyl-1H-imidazol-3-ium

1-{2-[(3-amino-7,8-dihydro-6H-cyclopenta[e]pyrazolo[1,5-a]pyridin-2-yl)amino]ethyl}-1-methylpyrrolidinium 1-{2-[(3-amino-7,8-dihydro-6H-cyclopenta[e]pyrazolo[1,5-a]pyridin-2-yl)amino]ethyl}-1-methylpiperidinium 4-{2-[(3-amino-7,8-dihydro-6H-cyclopenta[e]pyrazolo[1,5-a]pyridin-2-yl)amino]ethyl}-4-methylmorpholin-4-ium N-{2-[(3-amino-7,8-dihydro-6H-cyclopenta[e]pyrazolo[1,5-a]pyridin-2-yl)amino]ethyl}-N-isopropyl-N-methylpropan-2-aminium

-continued

[3-(3-Amino-4-dimethylamino-pyrazolo[1,5-a]pyridin-
2-ylamino)-propyl]-trimethyl-ammonium

[2-(3-Amino-4-dimethylamino-pyrazolo[1,5-a]pyridin-
2-ylamino)-ethyl]-trimethyl-ammonium

4-(3-Amino-4-dimethylamino-pyrazolo[1,5-a]pyridin-
2-yl)-1-methyl-piperazin-1-ium

[1-(3-Amino-4-dimethylamino-pyrazolo[1,5-a]pyridin-
2-yl)-pyrrolidin-3-yl]-trimethyl-ammonium 3-[2-(3-Amino-4-dimethylamino-pyrazolo[1,5-a]pyridin-
2-yloxy)-ethyl]-1-methyl-3H-imidazol-1-ium

[2-(3-Amino-4-dimethylamino-pyrazolo[1,5-a]pyridin-
2-yloxy)-ethyl]-trimethyl-ammonium

-continued

{1-[2-(3-Amino-4-dimethylamino-pyrazolo[1,5-a]pyridin-
2-yloxy)-ethyl]-pyrrolidin-3-yl}-trimethyl-ammonium (3-Amino-2-methanesulphonyl-pyrazolo[1,5-
a]pyridin-4-yl)-trimethyl-ammonium (3-Amino-2-methoxy-pyrazolo[1,5-
a]pyridin-4-yl)-trimethyl-ammonium In further embodiments, the at least one 3-aminopyrazolo[1,5-a]pyridine comprises 4-(3-aminopyrazolo[1,5-a]pyridin-2-yl)-1,1-dimethylpiperazin-1-ium chloride, dihydrochloride, which has a structure represented by formula (IVa):

The compounds of formula (IV) can be prepared by synthesis methods which are known in the literature, such as are described, for example, in the U.S. Pat. No. 7,578,855.

Reducing Agent

In one or more embodiments, the hair color-altering composition comprises one or more reducing agents. In one or more embodiments, the hair color-altering composition is substantially free, or free of thiolactic acid. As used herein, the term "reducing agent" refers to a chemical species which loses an electron to another chemical species in a redox chemical reaction.

Examples of reducing agents that are useful include, but are not limited to: sodium sulphite, anhydrous sodium thiosulfate, powdered sodium metabisulfite, thiourea, ammonium sulfite, thioglycolic acid, ammonium thiolactate, glyceryl monothioglycolate, ammonium thioglycolate, thioglycerol, 2,5-dihydroxybenzoic acid, diammonium dithioglycolate, strontium thioglycolate, calcium thiolgycolate, zinc formosulfoxylate, isooctyl thioglycolate, and monoethanolamine thiogylcolate. In one or more embodiments, the reducing agent comprises a monovalent thiolactate salt. In some embodiments, the monovalent thiolactate salt comprises ammonium thiolactate.

The reducing agent (e.g., ammonium thiolactate) may be present in amounts ranging from about 0.01, 0.05, 0.1, 0.2, 0.3, 0.4, 0.5, 0.6, 0.7 or 0.8 to about 0.3, 0.4, 0.5, 0.6, 0.7, 0.8, 0.9 or 1.0 wt. % by total weight of the composition.

Ammonia Compound

In one or more embodiments, the hair color-altering compositions comprise an ammonia compound. As used herein, the term "ammonia compound" refers to compounds which produce ammonia when in solution. Examples of such compounds include ammonia and compounds which may be added as ammonium hydroxide and ammonium salts (e.g., simple salts). As ammonium salts, mention may be made of inorganic ammonium salts such as ammonium carbonate, ammonium bicarbonate, ammonium chloride, ammonium nitrate, ammonium sulfate, ammonium phosphate; organic ammonium salts such as ammonium formate, ammonium acetate, and tetramethylammonium hydroxide; and mixtures thereof.

The hair color-altering agents described herein contain a relatively low amount of ammonia. In some embodiments, the ammonia compound may be about 0.01, 0.05, 0.1, 0.2, 0.3, 0.4, 0.5, 0.6, 0.7, 0.8, 0.9, 1.0, 1.5, 2.0, 2.5 or 3.0 to about 2.5, 3.0, 3.5, 4.0, 4.5 or 5.0 wt. % by total weight of the composition.

Alkanolamine

In one or more embodiments, the hair color-altering composition comprises one or more alkanolamines. Examples of alkanolamines include, but are not limited to, mono-, di- or trialkylamines, comprising one to three identical or different C1-C4 hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

Among the compounds of the alkanolamine type that may be mentioned include but not limited to: monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

As a non-limiting example, the organic amines are chosen from alkanolamines. For example, the organic amines are chosen from ethanolamine, triethanoloamine, 2-amino-2-methyl-1-propanol (amino methyl propanol), or preferably from 2-amino-2-methyl-1-propanol and monoethanolamine, or mixtures thereof. Further as an example, the organic amine is monoethanolamine.

The hair color-altering compositions described herein contain a relatively high amount of alkanolamine. The alkanolamine may be present in amounts ranging from about 5, 5.1, 5.2, 5.3, 5.4, 5.5, 5.6, 5.7, 5.8, 5.9, 6.0, 6.5, 7.0, 7.5 or 8.0 to about 5.6, 5.7, 5.8, 5.9, 6.0, 6.5, 7.0, 7.5, 8.0, 8.5, 9.0, 9.5 or 10 wt. % by total weight of the composition.

Carboxylic Acid-Containing Surfactant

In one or more embodiments, the hair color-altering compositions comprise a carboxylic acid-containing surfactant. Examples of such include alkyl ether carboxylic acids (e.g., polyoxyethylene alkylether carboxylic acids). Examples include, but are not limited to, Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-C15 Pareth-7 Carboxylic Acid, C12-C13 Pareth-5 Carboxylic Acid, C12-C13 Pareth-8 Carboxylic Acid, C12-13 Pareth-12 Carboxylic Acid, C12-C15 Pareth-7 Carboxylic Acid, C12-C15 Pareth-8 Carboxylic Acid, C14-C15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid.

The hair color-altering agents described herein contain a relatively low amount of ammonia. In some embodiments, the ammonia compound may be about 0.01, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5 or 3.0 to about 2.5, 3.0, 3.5, 4.0, 4.5, 5.0, 5.5 or 6.0 wt. % by total weight of the composition.

Antioxidant

As used herein, the term "antioxidant" refers to a molecule that inhibits the oxidation of another molecule by itself being oxidized. In some embodiments, the antioxidant comprises ascorbic acid, sodium sulfite, sodium metabisulfite, sodium hydrosulfite, tocopherols, alpha-tocopherol, tocopheryl acetate, panthenol, selenium sulfide, zinc formosulfoxylate, isoascorbic acid, magnesium ascorbyl phosphate, ascorbyl glucoside, cysteine, thiourea, glyceryl monothioglycolate, thioglycerol, 2,5-dihydroxybenzoic acid, erythorbic acid and combinations thereof.

The antioxidant (e.g., erythorbic acid) may be present in amounts ranging from about 0.01, 0.05, 0.1, 0.2, 0.3, 0.4, 0.5, 0.6, 0.7 or 0.8 to about 0.1, 0.2, 0.3, 0.4, 0.5, 0.6, 0.7, 0.8, 0.9 or 1.0 wt. % by total weight of the composition.

Additional Dyes

In some embodiments, the hair color-altering composition may further comprise additional dyes. In one or more embodiments, the additional dyes may be selected from one or more oxidation dyes. In embodiments comprising oxidation dyes, the oxidation dyes are generally chosen from one or more oxidation bases optionally combined with one or more couplers. By way of example, the oxidation bases may be chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β- acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases can include additional 3-aminopyrazolo[1,5-a]pyridine oxidation bases or the addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-□-hydroxyethoxy-3-amino-pyrazolo[1,5-a]pyridine; 2-(4-diméthylpyperazinium-1-yl)-3-amino-pyrazolo[1,5-a]pyridine; and the addition salts thereof.

More particularly, oxidation bases can be selected from 3-aminopyrazolo-[1,5-a]-pyridines and preferably substituted on carbon atom 2 by:
(a) one (di)($C_1$-$C_6$)(alkyl)amino group wherein said alkyl group can be substituted by at least one hydroxy, amino, imidazolium group;
(b) one heterocycloalkyl group containing from 5 to 7 members chain, and from 1 to 3 heteroatomes, potentially cationic, potentially substituted by one or more ($C_1$-$C_6$)alkyl, such as di($C_1$-$C_4$)alkylpipérazinium; or
(c) one ($C_1$-$C_6$)alkoxy potentially substituted by one or more hydroxy groups such as α-hydroxyalkoxy, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof. 4,5-Diamino-1-(β-methoxyethyl)pyrazole may also be used. A 4,5-diaminopyrazole will preferably be used, and even more preferentially 4,5-diamino-1-(β-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one.

2,3-Diamino-6,7-dihydro-1H,5H-pyrazolo[1,2-a]pyrazol-1-one and/or a salt thereof will preferably be used. 4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Compositions and/or systems according to embodiments of the disclosure may optionally further comprise one or more couplers advantageously chosen from those conventionally used in the dyeing or coloring of keratinous substrates.

Among these couplers, mention may be made especially of meta-phenylenediamines, meta-aminophenols, meta-diphenols, naphthalene-based couplers and heterocyclic couplers, and also the addition salts thereof.

Mention may be made, for example, of 2-methyl-5-aminophenol, 5-N-(β-hydroxyethyl)amino-2-methylphenol, 3-aminophenol, 5-amino-6-chloro-o-cresol (3-amino-2-chloro-6-methylphenol), 1,3-dihydroxybenzene, 1,3-dihydroxy-2-methyl-benzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)-toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the invention are especially selected from the addition salts with an acid such as the hydrochlorides, hydrobromides, sulfates, citrates, succinates, tartrates, lactates, tosylates, benzenesulfonates, phosphates and acetates.

The oxidation base(s) may be present in an amount ranging from about 0.001% to 10% by weight, such as from about 0.005% to 5% by weight, relative to the total weight of the system or composition comprising the system in which it is present.

The coupler(s), if they are present, may be present in an amount ranging from about 0.001% to 10% by weight, such as from about 0.005% to 5% by weight, relative to the total weight of the system or composition comprising the system in which it is present.

Solvent

In one or more embodiments, the hair color-altering compositions described herein comprise a solvent. In some embodiments, the solvent comprises water. The total amount of water in the hair color-altering compositions may vary depending on the type of composition and the desired consistency, viscosity, etc. In some cases, the total amount of water is about 0.1 to 60 wt. %, based on the total weight of the hair color-altering composition, including all ranges and subranges therebetween. The total amount of water may be about 20 to about 50 wt. %. In one or more embodiments, the total amount of water may be at least 5, 10, 15, 20, 25, 30, 35, or 40 wt. % to about 35, 40, 45, 50, 55 or 60 wt. %.

In some embodiments, the composition may comprise other solvents, for example, glycerin, $C_{1-4}$ alcohols, organic solvents, fatty alcohols, fatty ethers, fatty esters, polyols, glycols, vegetable oils, mineral oils, liposomes, laminar lipid materials, or any a mixture thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, propylene glycol, caprylyl glycol, glycerin, isopropyl alcohol, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof.

Polyol compounds may also be used. Non-limiting examples include the aliphatic diols, such as 2-ethyl-2- methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the water-soluble solvents (which is separate than the water in the compositions) may vary, but in some cases are about 0.01 to about 50 wt. %, based on the total weight of the composition. The total amount of the water-soluble solvents (separate from the water in the compositions), is about 0.01 to about 40 wt. %, about 0.01 to about 30 wt. %, about 0.01 to about 20 wt. %, about 0.01 to about 10 wt. %, about 0.01 to about 5 wt. %, 0.1 to about 40 wt. %, about 0.1 to about 30 wt. %, about 0.1 to about 20 wt. %, about 0.1 to about 10 wt. %, or about 0.1 to about 5 wt. %.

Optional Components

The composition according to the disclosure can comprise any auxiliary or additional component suitable for use in cosmetic compositions, and in particular suitable for hair coloring or lightening compositions. Such components may include, but are not limited to, cosmetically acceptable solvents, silicone compounds, rheology modifying agents such as acrylic polymers, cationic, nonionic, amphoteric or zwitterionic surfactants or mixtures thereof, anionic, cationic, nonionic, amphoteric or zwitterionic polymers or mixtures, film forming agents or polymers, humectants and moisturizing agents, fatty substances other than the claimed fatty substances, emulsifying agents other than fatty substances, fillers, structuring agents, propellants, shine agents, conditioning agents, antioxidants or reducing agents, penetrants, sequestrants, fragrances, buffers, dispersants, conditioning agents, for instance volatile or non-volatile, modified or unmodified silicones, ceramides, preserving agents, opacifiers, sunscreen agents, and antistatic agents. As such, optional auxiliary or additional components will be chosen so as to minimize any detrimental effect to the advantages of the hair color bases and compositions described herein.

Exemplary auxiliary ingredients useful in the hair color composition according to various embodiments of the disclosure include, but are not limited to, rheology-modifying agents, bleach activators and co-bleach activators, direct dyes, chelants, fatty substances, ceramides, alkoxyaminosilicones, silanes, and lift-enhancing agents, such as nitrogen-containing compounds and metal catalyst compounds.

In some embodiments, the hair color-altering compositions comprise at least one surfactant in addition to the carboxylic acid-containing surfactant. In such embodiments, the additional surfactant(s) are selected from anionic surfactants, nonionic surfactants and mixtures thereof.

In one or more embodiments, the hair color base composition is essentially free or free of a polyquaternium polymer. Such polyquaternium polymers are cationic. In one or more embodiments, the polyquaternium polymer is selected from the group consisting of polyquaternium-6, polyquaternium-22 or polyquaternium-5.

The total amount of the one or more surfactants included in the hair color-altering compositions can vary, especially depending on the type of hair color-altering composition in with they are contained. The total amount of the one or more surfactants is typically about 0.1 to about 40 wt. %, based on the total weight of the hair color-altering composition, including all ranges and subranges therebetween. In some cases, the total amount of the one or more surfactants is about 0.1 to about 35 wt. %, about 0.1 to about 30 wt. %, about 0.1 to about 25 wt. %, about 0.1 to about 20 wt. %, about 0.1 to about 15 wt. %, about 0.1 to about 10 wt. %, about 0.1 to about 5 wt. %, about 0.5 to about 40 wt. %, about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 0.5 to about 5 wt. %, about 1 wt. % to about 40 wt. %, about 1 wt. % to about 30 wt. %, about 1 wt. % to about 20 wt. %, about 1 wt. % to about 15 wt. %, about 1 wt. % to about 10 wt. %, or about 1 wt. % to about 5 wt. %.

The composition may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The pH adjusters may, in various embodiments, be present in the hair color composition in an amount effective with a pH of greater than 7.

Kits

Another aspect of the invention pertains to kits which comprise any of the hair color-altering agents described herein. In some embodiments, the kit further comprises a developer composition. The developer composition may be housed in a separate container from the hair color-altering composition, and may then be mixed prior to application onto hair.

In some embodiments, the developer composition is aqueous or is in the form of an emulsion. The developer composition can contain at least one solvent, chosen from water, organic solvents, and mixtures thereof.

In various exemplary embodiments, hydrogen peroxide is present in an amount of at least about 1% by weight, based on the total weight of the developer composition. In further embodiments, hydrogen peroxide is present in an amount ranging from about 0.1% to about 80% by weight, such as from about 1.0% to about 75% by weight, or from about 2% to about 10% by weight, based on the total weight of the developer composition. In further exemplary embodiments, the hydrogen peroxide may be present in the developer composition in an amount ranging from about 2% to about 25%, such as about 4% to about 20%, about 6% to about 15%, or about 7% to about 10%.

The cosmetically acceptable carrier of the developer composition may, for example, be present in an amount ranging from about 0.5% to about 99% by weight, such as from about 5% to about 95% by weight, relative to the total weight of the developer composition.

In alternative embodiments, the developer composition is substantially anhydrous. The term "substantially anhydrous" means that the developer composition is either completely free of water or contains no appreciable amount of water, for example, no more than 5% by weight, or no more than 2% by weight, or no more than 1% by weight, based on the weight of the developer composition. It should be noted that this refers for example to bound water, such as the water of crystallization of the salts or traces of water absorbed by the raw materials used in the preparation of the compositions according to embodiments of the disclosure.

When the developer composition is substantially anhydrous, the developer composition may comprise at least one solvent chosen from organic solvents. Suitable organic solvents for use in the developer composition include ethanol, isopropyl alcohol, propanol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, ethylene glycol, propylene glycol, butylene glycol, hexylene glycol, propane diol, glycerin, hydrocarbons such as straight chain hydrocarbons, mineral oil, polybutene, hydrogenated polyisobutene, hydrogenated polydecene, polydecene, squalane, petrolatum, isoparaffins, and mixtures, thereof.

The developer composition may be in the form of a powder, gel, liquid, foam, lotion, cream, mousse, and emulsion.

The pH of the developer composition can range from about 2 to about 12, such as from about 3 to about 7, and it may be adjusted to the desired value using acidifying/alkalizing agents that are well known in the art. In certain embodiments, the pH of the developer composition is below 7. The pH of the composition resulting from mixing together the hair color-altering composition and the developer composition may range from about 7, 8, 9, 10 or 11 to about 8, 9, 10, 11 or 12.

Methods

Another aspect of the invention pertains to methods of using any of the compositions described herein. In one or more embodiments, the method comprises applying the hair color-altering composition to hair. The composition may be left on the hair for a period of time sufficient to achieve the desired alteration in hair tone. For example, the hair color composition may be left on the hair for up to one hour, such as from about 3 minutes to about 45 minutes, from about 5 minutes to about 30 minutes, or from about 10 minutes to about 20 minutes. In further embodiments, the hair color composition may be left on the hair for a period up to about 30 minutes, such as, for example, from about 1 to about 30 minutes, about 1 to about 10 minutes, or about 1 to about 5 minutes. One skilled in the art will, by considering various factors such as the starting and desired tones of the hair, be able to determine an appropriate amount of time to leave the hair color composition on the hair in order to achieve the desired alternation in hair tone. In some embodiments, the hair color-altering composition is mixed with a developer composition prior to application to hair. If desired, the composition may, optionally, be shampooed and/or rinsed off the hair.

Form

The hair color-altering compositions of the instant disclosure can be in a variety of forms. For example, in many instances, the hair color-altering compositions are in the form of a liquid, gel, lotion, creme, and/or spray. The hair color-altering compositions may be packaged in a variety of different containers, such as, for example, a ready-to-use container. Non-limiting examples of useful packaging include tubes, jars, caps, unit dose packages, and bottles, including squeezable tubes and bottles.

EXAMPLES

Implementation of the present disclosure is provided by way of the following examples. The examples serve to illustrate the technology without being limiting in nature.

Example 1—Reducing Agent

Three formulas were prepared with the ingredients shown below in Table 1. Example 1 is a clear base, so it does not contain dye. Example 2 contains dye. Example 3 is comparative, as it contains thiolactic acid.

In a flask, the surfactants, solvents, and fatty compounds were combined with water and mixed until all solids were dissolved. The reducing agent was added and the mixture mixed for 5 minutes. The chelants, antioxidants and dyes (if present, other than hydroxyethoxy aminopyrazolopyridine HCl) and additional water were added. The mixture was mixed at high speed for about 15 minutes until solids were dissolved. Hydroxyethoxy aminopyrazolopyridine HCl (if present) was then added and mixed for 15 minutes. The batch was then left to rest for about 30 minutes until it became transparent. Fragrance was then added and the batch mixed for 2 minutes. Monoethanolamine was then added and the batch mixed for 5 minutes. Finally, ammonium hydroxide was added and the batch mixed for an additional 5 minutes. The batch was then covered with foil and allowed to rest for 15-30 minutes to become a transparent liquid.

TABLE 1

| CLAIM ELEMENT | INGREDIENT | EX. 1 (CLEAR) | EX. 2 (SHADE 5.6) | EX. 3 (COMP.) |
|---|---|---|---|---|
| (b) | AMMONIUM THIOLACTATE | 0.464 | 0.464 | |
| | THIOLACTIC ACID | | | 0.251 |
| (a) | HYDROXYETHOXY AMINOPYRAZOLO-PYRIDINE HCL | | 1.25 | 1.25 |
| | WATER | 41.2003 | 38.5573 | 38.7703 |
| (f) | ERYTHORBIC ACID | 0.31 | 0.31 | 0.31 |
| (c) | AMMONIUM HYDROXIDE | 1.2345 | 1.2345 | 1.2345 |
| (d) | MONOETHANOLAMINE | 5.66 | 5.66 | 5.66 |
| (e) | LAURETH-5 CARBOXYLIC ACID | 4.5 | 4.5 | 4.5 |
| | OTHER DYE COMPOUNDS | | 1.393 | 1.393 |
| | OTHER SURFACTANTS | 24.0602 | 24.0602 | 24.0602 |
| | SOLVENTS | 20.32 | 20.32 | 20.32 |
| | MISC (FRAGRANCE, CHELANT, FATTY COMPOUND) | 2.251 | 2.251 | 2.251 |
| | TOTAL | 100 | 100 | 100 |

Stability of Inventive Example 2 and Comparative Example 3 was evaluated, with results shown in Table 2 below.

TABLE 2

| | 24 Hours | 1 month 45° C. | 1 month Room Temp. | 2 month 45° C. | 2 month Room Temp. |
|---|---|---|---|---|---|
| Inv. Ex. 2 | Stable: Transparent, yellow liquid | Stable: 5/5 jars normal orange | Stable: 1/1 jars normal | Stable: 5/5 jars normal orange | Stable: 1/1 jars normal orange liquid |
| Comp. Ex. 3 | Unstable: cloudy, non-homogenous, yellow particles throughout and yellow precipitate layer on bottom | Cannot be batched - unstable | Cannot be batched - unstable | Cannot be batched - unstable | Cannot be batched - unstable |

As seen from Table 2, comparative formula could not be batched and is unstable T24. In contrast, the inventive Formula was stable at 2 months at 45 C and 25 C.

Example 2—Color Longevity

Three formulas were prepared with the ingredients shown below in Table 2 via the same process described in Example 1. Examples 1-3 are inventive.

TABLE 3

| CLAIM ELEMENT | INCI US | Ex. 4 (Shade 4R) | Ex. 5 (Shade 5.21) | Ex. 6 (Shade 4.15) |
|---|---|---|---|---|
| (a) | HYDROXYETHOXY AMINOPYRAZOLO-PYRIDINE HCL | 0.4 | 0.25 | 0.2 |
| (e) | LAURETH-5 CARBOXYLIC ACID | 4.5 | 4.5 | 4.5 |
| | FRAGRANCE | 0.95 | 0.8 | 0.8 |
| (c) | AMMONIUM HYDROXIDE | 1.2345 | 1.2345 | 1.2345 |
| (b) | AMMONIUM THIO-LACTATE | 0.464 | 0.464 | 0.464 |
| (d) | ETHANOLAMINE | 5.66 | 5.66 | 5.66 |
| | WATER | 39.3703 | 39.7553 | 39.0203 |
| (f) | ERYTHORBIC ACID | 0.31 | 0.31 | 0.31 |
| | OTHER DYE COMPOUNDS | 1.431 | 1.346 | 2.131 |
| | OTHER SURFACTANTS | 24.0602 | 24.0602 | 24.0602 |
| | OTHER SOLVENTS | 20.32 | 20.32 | 20.32 |
| | MISC. (CHELANT, FATTY COMPOUND) | 1.3 | 1.3 | 1.3 |

Two sets of hair swatches (permed and unpermed) were treated with the formulations of Ex. 4-6 and LAB values were taken. These were compared to commercially available hair color bases with the equivalent shade (Comparative Ex. 7-9). The color base was mixed with 25V developer in a 1:1.5 ratio. The mixture was then applied to the swatches and then allowed to process for approximately 25 minutes. The swatches were then rinsed with water until the water ran clear. Excess water was then removed, followed by shampoo.

Figure 1:
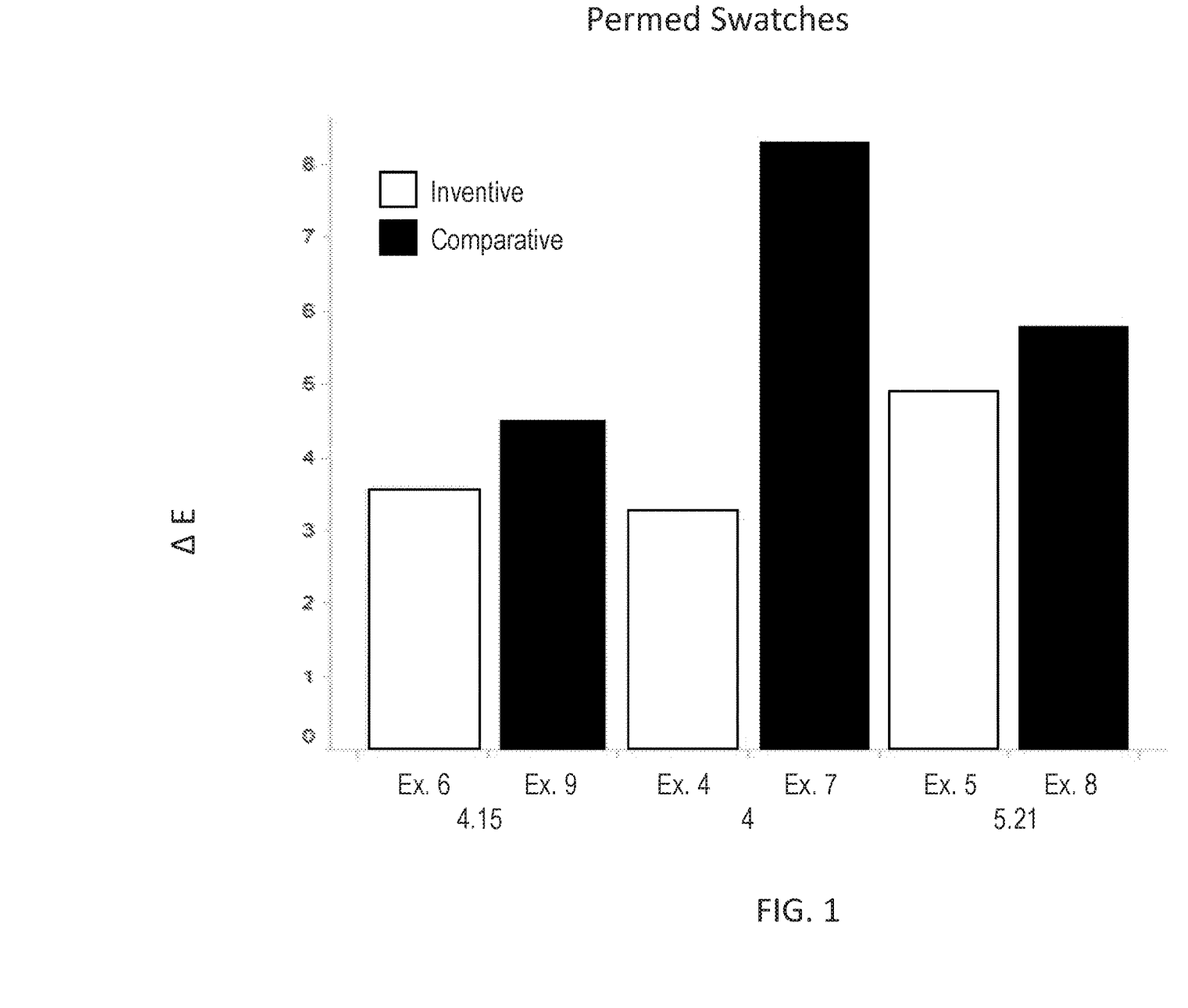
FIG. 1 shows the ΔE after 14 washes of permed hair after treatment with three hair color-altering compositions according to one or more embodiments of the invention as well as three comparative compositions.
Figure 2:
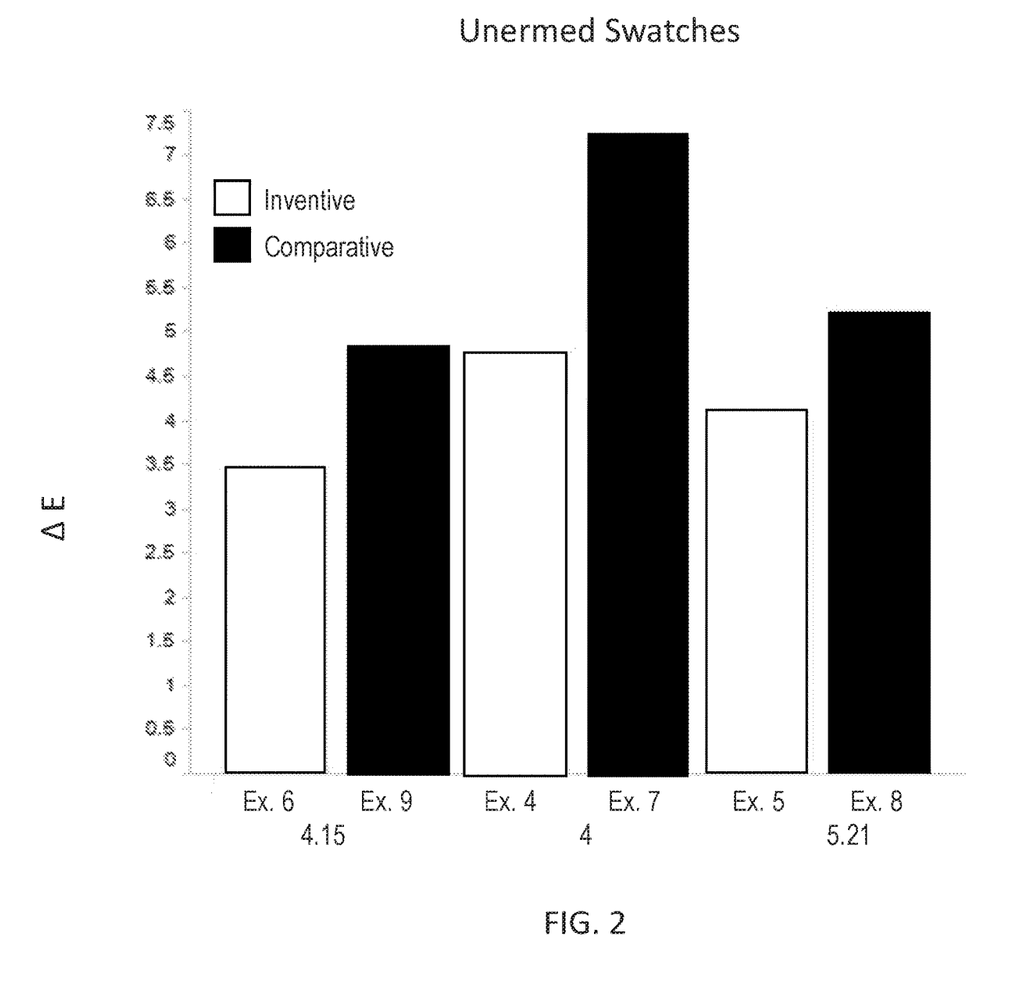
FIG. 2 shows the ΔE after 14 washes of unpermed hair after treatment with three hair color-altering compositions according to one or more embodiments of the invention as well as three comparative compositions.

FIG. 1 shows the ΔE for permed hair swatches treated with Examples 4-9 after 14 shampoos. FIG. 2 shows the ΔE for unpermed hair swatches treated with Examples 4-9 after 14 shampoos. As can be seen from the figures, the inventive examples consistently provide lower ΔE values, indicating less of a color shift after 14 shampoos. This shows the inventive formulas have better color longevity.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, E, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts, for example, the salts of the amino acids, the amino sulfonic acids, and the non-polymeric mono, di, and/or tricarboxylic acids, which are referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

"Keratinous substrates" as used herein, includes, but is not limited to keratin fibers such as hair and/or scalp on the human head.

"Conditioning" as used herein means imparting to one or more hair fibers at least one property chosen from combability, moisture-retentivity, luster, shine, and softness. The state of conditioning can be evaluated by any means known in the art, such as, for example, measuring, and comparing, the ease of combability of the treated hair and of the untreated hair in terms of combing work (gm-in), and consumer perception.

The term "treat" (and its grammatical variations) as used herein refers to the application of the compositions of the present disclosure onto the surface of keratinous substrates such as hair. The term 'treat" (and its grammatical variations) as used herein also refers to contacting keratinous substrates such as hair with the compositions of the present disclosure.

A "rinse-off" product refers to a composition such as a hair color-altering composition that is rinsed and/or washed with water either after or during the application of the composition onto the keratinous substrate, and before drying and/or styling said keratinous substrate. At least a portion, and typically most, of the composition is removed from the keratinous substrate during the rinsing and/or washing.

The term "stable" as used herein means that the composition does not exhibit phase separation and/or crystallization for a period of time, for example, for at least 1 day (24 hours), one week, one month, or one year.

"Volatile", as used herein, means having a flash point of less than about 100° C.

"Non-volatile", as used herein, means having a flash point of greater than about 100° C.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3 wt. %, less than about 2 wt. %, less than about 1 wt. %, less than about 0.5 wt. %, less than about 0.1 wt. %, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair color-altering composition comprising:
    (a) about 0.05 to about 10 wt. % of at least one 3-aminopyrazolo[1,5-a]pyridine;
    (b) from about 0.01 to about 1 wt. % of a reducing agent other than thiolactic acid that is a monovalent thiolactate salt;
    (c) from about 0.01 to about 5 wt. % of an ammonia compound;
    (d) from about 5 to about 10 wt. % of an alkanolamine;
    (e) from about 0.01 to about 6 wt. % of a carboxylic acid-containing surfactant; and
    (f) from about 0.01 to about 1 wt. % of an antioxidant.

2. The hair color-altering composition of claim 1, wherein the hair color-altering composition is in the form of a microemulsion.

3. The hair color-altering composition of claim 1, wherein the at least one 3-aminopyrazolo[1,5-a]pyridine is present in an amount of about 0.4 to about 2.5 wt. %.

4. The hair color-altering composition of claim 1, wherein the at least one 3-aminopyrazolo[1,5-a]pyridine comprises 2-[(3-aminopyrazolo[1,5-a]pyridin-2-yl)oxy]ethanol hydrochloride.

5. The hair color-altering composition of claim 1, wherein the at least one 3-aminopyrazolo[1,5-a]pyridine comprises 4-(3-Amino-pyrazolo[1,5-a]pyridin-2-yl)-1,1-dimethyl-piperazin-1-ium or a salt thereof.

6. The hair color-altering composition of claim 1, wherein the monovalent thiolactate salt comprises ammonium thiolactate.

7. The hair color-altering composition of claim 1, wherein the ammonia compound comprises ammonium hydroxide.

8. The hair color-altering composition of claim 1, wherein the alkanolamine is present in an amount of from about 5 to about 8 wt. %.

9. The hair color-altering composition of claim 1, wherein the alkanolamine comprises monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane, and combinations thereof.

10. The hair color-altering composition of claim 9, wherein the alkanolamine comprises monoethanolamine.

11. The hair color-altering composition of claim 1, wherein the antioxidant comprises ascorbic acid, sodium sulfite, sodium metabisulfite, sodium hydrosulfite, tocopherols, alpha-tocopherol, tocopheryl acetate, panthenol, selenium sulfide, zinc formosulfoxylate, isoascorbic acid, magnesium ascorbyl phosphate, ascorbyl glucoside, cysteine, thiourea, glyceryl monothioglycolate, thioglycerol, 2,5-dihydroxybenzoic acid, erythorbic acid and combinations thereof.

12. The hair color-altering composition of claim 1, wherein the carboxylic acid-containing surfactant comprises laureth-11 carboxylic acid, laureth-5 carboxylic acid, and combinations thereof.

13. The hair color-altering composition of claim 1, wherein the composition is essentially free of a polyquaternium polymer.

14. The hair color-altering composition of claim 13, wherein the composition is essentially free of polyquaternium-6.

15. The hair color-altering composition of claim 1, wherein the composition is stable for at least one month.

16. The hair color-altering composition of claim 1, wherein the composition is essentially free of thiolactic acid.

17. A hair color-altering composition comprising:
    (a) about 0.05 to about 10 wt. % of 2-[(3-aminopyrazolo[1,5-a]pyridin-2-yl)oxy]ethanol hydrochloride;
    (b) from about 0.01 to about 1 wt. % of ammonium thiolactate;
    (c) from about 0.01 to about 5 wt. % of ammonia;
    (d) from about 5 to about 10 wt. % of an monoethanolamine;
    (e) from about 0.01 to about 6 wt. % of laureth-5 carboxylic acid; and
    (f) from about 0.01 to about 1 wt. % of erythorbic acid.

18. A kit comprising the hair color-altering composition of claim 1 and a developer composition comprising one or more oxidizing agents.

19. A method of coloring hair, the method comprising applying the hair color-altering composition of claim 1 to hair.

* * * * *